United States Patent [19]

Miwa et al.

[11] Patent Number: 5,532,769
[45] Date of Patent: Jul. 2, 1996

[54] OPHTHALMOLOGIC ALIGNMENT DEVICE WITH AUTOMATIC ALIGNMENT MEANS

[75] Inventors: Tetsuyuki Miwa, Aichi-ken; Munehiro Nakao, Toyokawa; Nobuo Suzuki, Aichi-ken; Koki Kato, Anjo, all of Japan

[73] Assignee: Nidek Co., Ltd., Aichi-ken, Japan

[21] Appl. No.: 406,403

[22] Filed: Mar. 20, 1995

[30] Foreign Application Priority Data

Mar. 31, 1994 [JP] Japan .................................. 6-087589
Jun. 30, 1994 [JP] Japan .................................. 6-173579
Jun. 30, 1994 [JP] Japan .................................. 6-173580

[51] Int. Cl.$^6$ ....................................................... A61B 3/10
[52] U.S. Cl. ........................... 351/205; 351/208; 351/221
[58] Field of Search ................................... 351/205, 208, 351/221, 245, 246

[56] References Cited

U.S. PATENT DOCUMENTS

| | | | |
|---|---|---|---|
| 4,813,778 | 3/1989 | Madate et al. | 351/208 |
| 4,881,807 | 11/1989 | Luce et al. | 351/208 |
| 5,252,821 | 10/1993 | Sugimura | 250/22 |
| 5,381,194 | 1/1995 | Nishio et al. | 351/208 |

Primary Examiner—William L. Sikes
Assistant Examiner—James A. Duclek
Attorney, Agent, or Firm—Nikaido Marmelstein Murray & Oram

[57] ABSTRACT

An ophthalmologic alignment device for aligning a measuring system at a predetermined position for an eye to be examined. The user moves the measuring system with a joystick for aligning purposes while observing a frontal eye image with an observation unit. A second moving unit further moves the measuring system moved by the user. An index projection/detection system projects an index onto the eye and detects the reflected index. The controller causes drivers to drive the second moving unit on the basis of the result of the detection of the index projection/detection system. A mode switch switches the movement of the measuring system from a mode in which the observation unit is moved by the first moving unit to a mode in which the observation unit is moved by the second moving unit, whereby the alignment of the eye and the measuring system is achieved easily and with high accuracy, irrespective of the degree of the user's skillfulness in handling the alignment device.

10 Claims, 9 Drawing Sheets

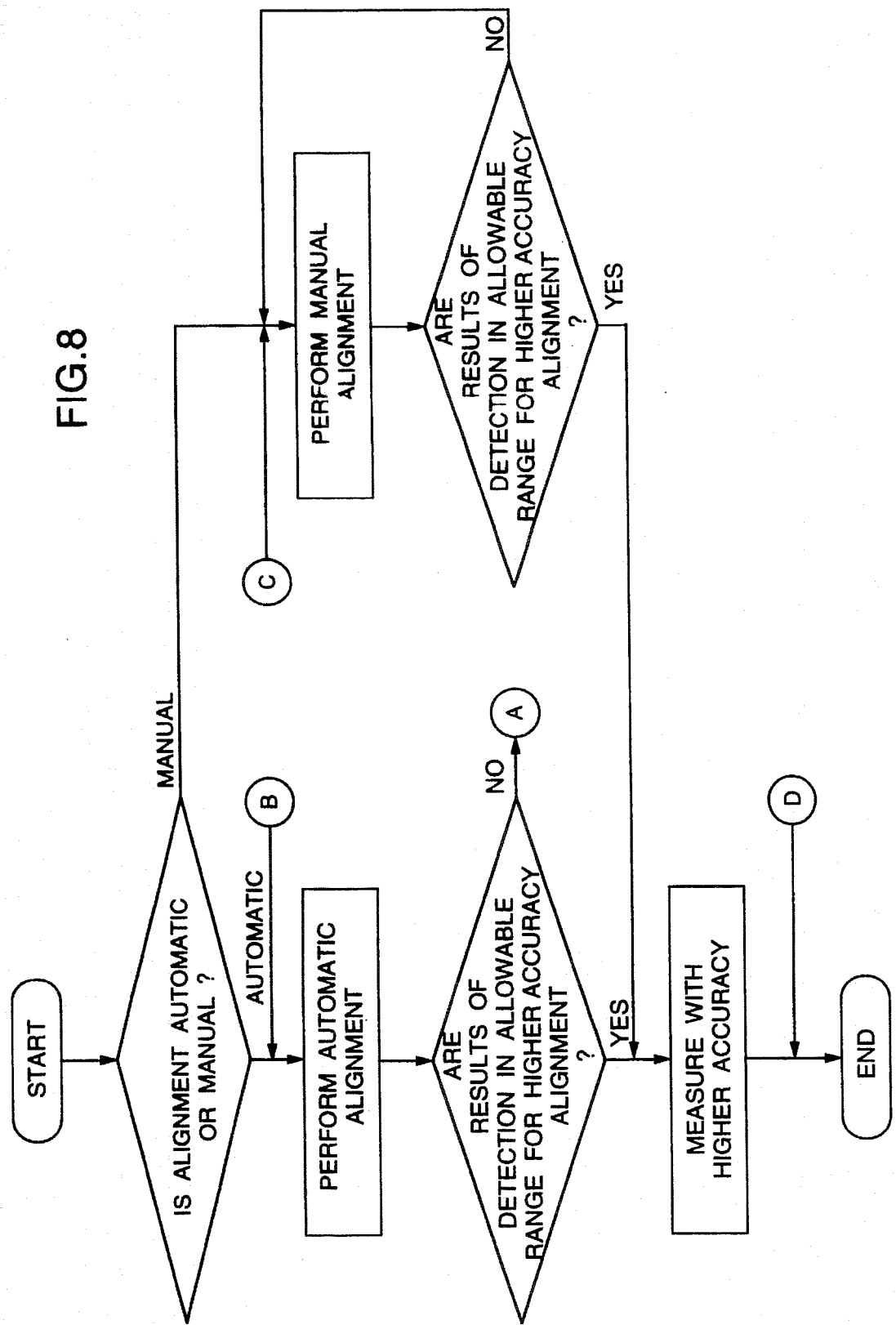

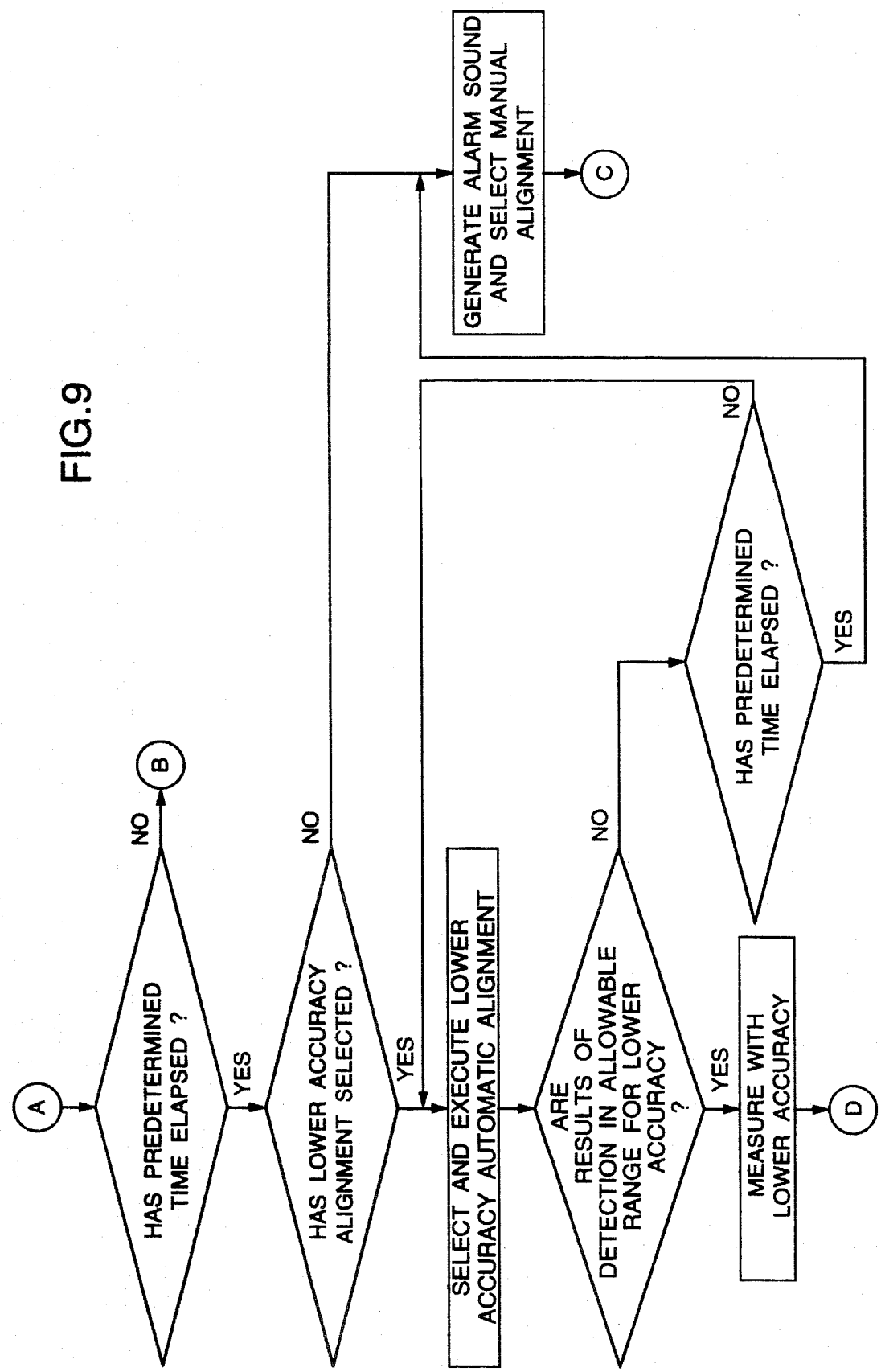

OPHTHALMOLOGIC ALIGNMENT DEVICE WITH AUTOMATIC ALIGNMENT MEANS

BACKGROUND OF THE INVENTION

The present invention relates to ophthalmologic devices, and more particularly to an apparatus which aligns a measuring system of an ophthalmologic device with high accurately with a respective one of eyes to be examined such that the measuring system is in a predetermined positional relationship to the eye.

An ophthalmologic device such as a non-contact tonometer or an objective eye refractivity measuring device, and more particularly its measuring system are required to be aligned vertically and horizontally and in distance with a respective one of the eyes to be examined, for measuring purposes, such that the device is put finally in a predetermined positional relationship to the respective one of the eyes.

Conventionally, an alignment mechanism for an ophthalmologic device is known which projects an alignment index image to a respective one of the eyes to be examined, receives a reflected image of a vetex cornea of the eye along with a frontal eye image in an observation unit, and drives a sliding mechanism, for example with a joystick, while viewing a television monitor, such that an optical system of the observation unit is placed in a predetermined positional relationship to the eye. U.S. Pat. No. 5,252,821, U.S. Ser. No. 08/076,745, and U.S. Ser. No. 08/052,916, have been known as prior arts.

The user is required to manipulate the joystick while viewing the TV monitor in the alignment. Thus, when the user is not used to align an ophthalmologic device such as a non-contact tonometer which requires an especially high accuracy of alignment, however, it would take much time for the user to perform the alignment and its accuracy would not be sufficiently high.

In order to handle a device which requires high accuracy of alignment, the user is required to be skilful in the manipulation of the device, and hence to be trained sufficiently to achieve satisfactorily complete manipulation of the device.

SUMMARY OF THE INVENTION

It is therefore an object of the present invention to provide an ophthalmologic alignment device which is capable of easily and with high accuracy achieving the alignment between the device and a respective one of the eyes to be examined irrespective of the degree of user's skillfulness in handling the device.

In order to achieve the above object, the present invention provides an ophthalmologic alignment device for aligning a measuring system at a predetermined position for an eye to be examined, including:

observation means for observing the front of the eye;

first moving means for moving the measuring system with a joystick for aligning purposes while observing the eye with the observation means;

second moving means for further moving the measuring system moved by the first moving means;

index projection/detection means for projecting an index onto the eye and detecting the projected index;

drive/control means for driving/controlling the second moving means on the basis of the result of the detection of the index projection/detection means; and mode switching means for switching an alignment mode in which the measuring system is moved from an alignment mode in which the measuring system is moved by the first moving means to an alignment mode in which the measuring system is moved by the second moving means.

Figure 6:
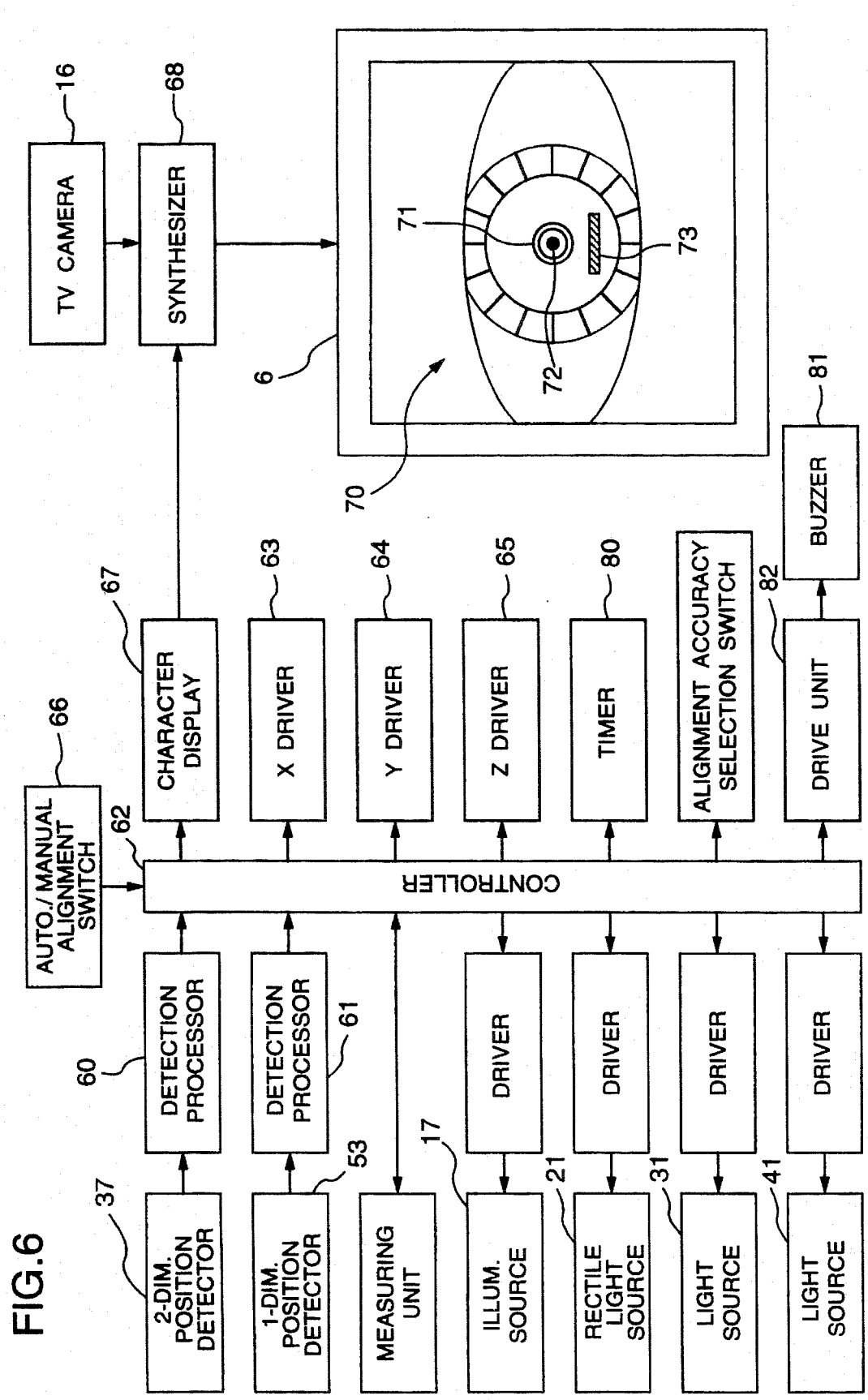
Figure 7:
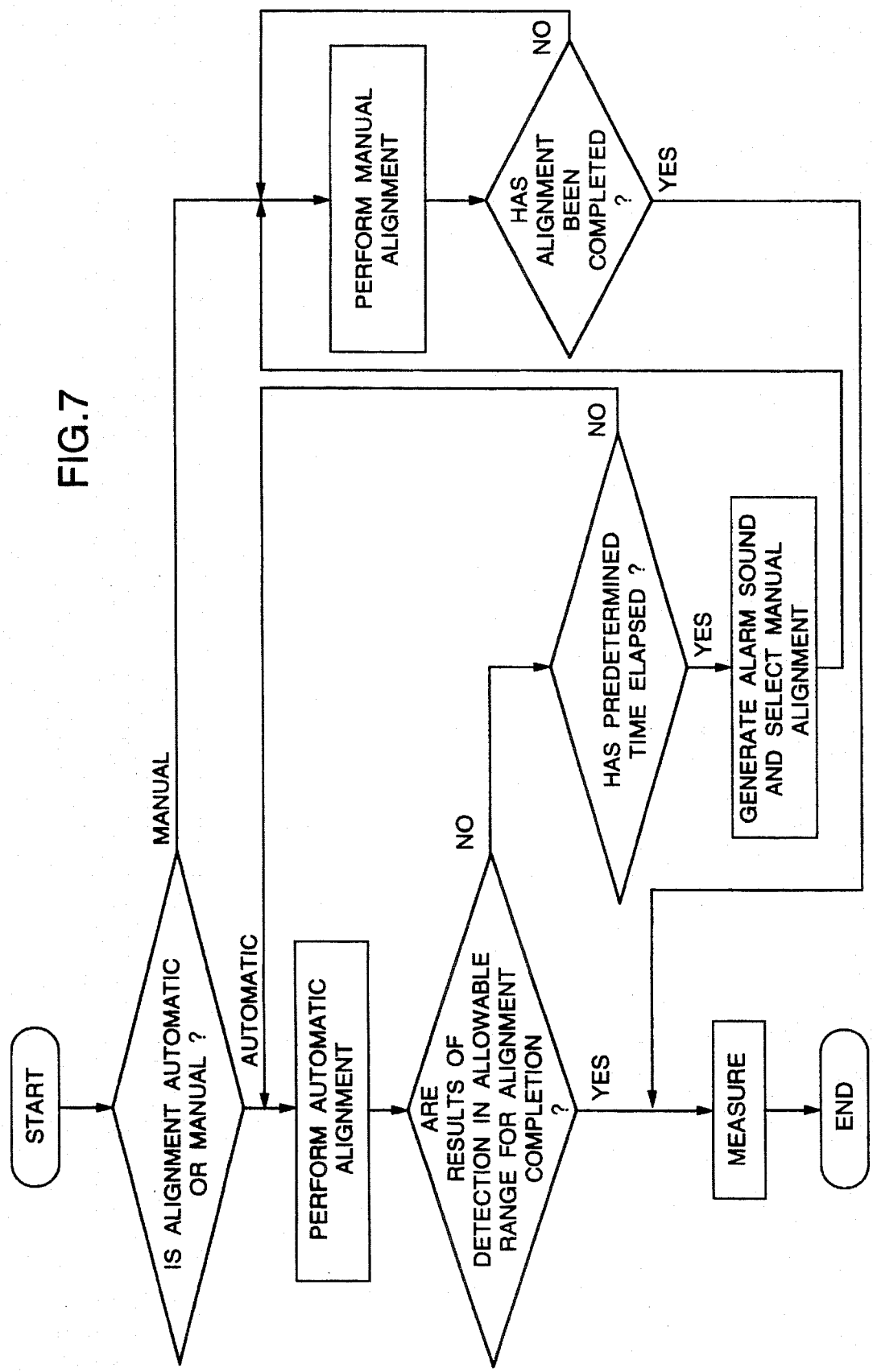

is a block digram of an essential portion of a control system of the embodiment;

FIG. 6 is a block diagram of an essential portion of a control system of the embodiment;

FIG. 7 is a flowchart indicative of the operation of the embodiment;

FIG. 8 is a flowchart indicative of the operation of the embodiment performed when same has an allowable range of low accuracy; and FIG. 9 is a flowchart to be combined with the flowchart of FIG. 8.

DESCRIPTION OF THE PREFERRED EMBODIMENTS

A preferred embodiment of an non-contact tonometer according to the present invention will be described below with reference to the drawings.

[Whole Structure]

Figure 1:
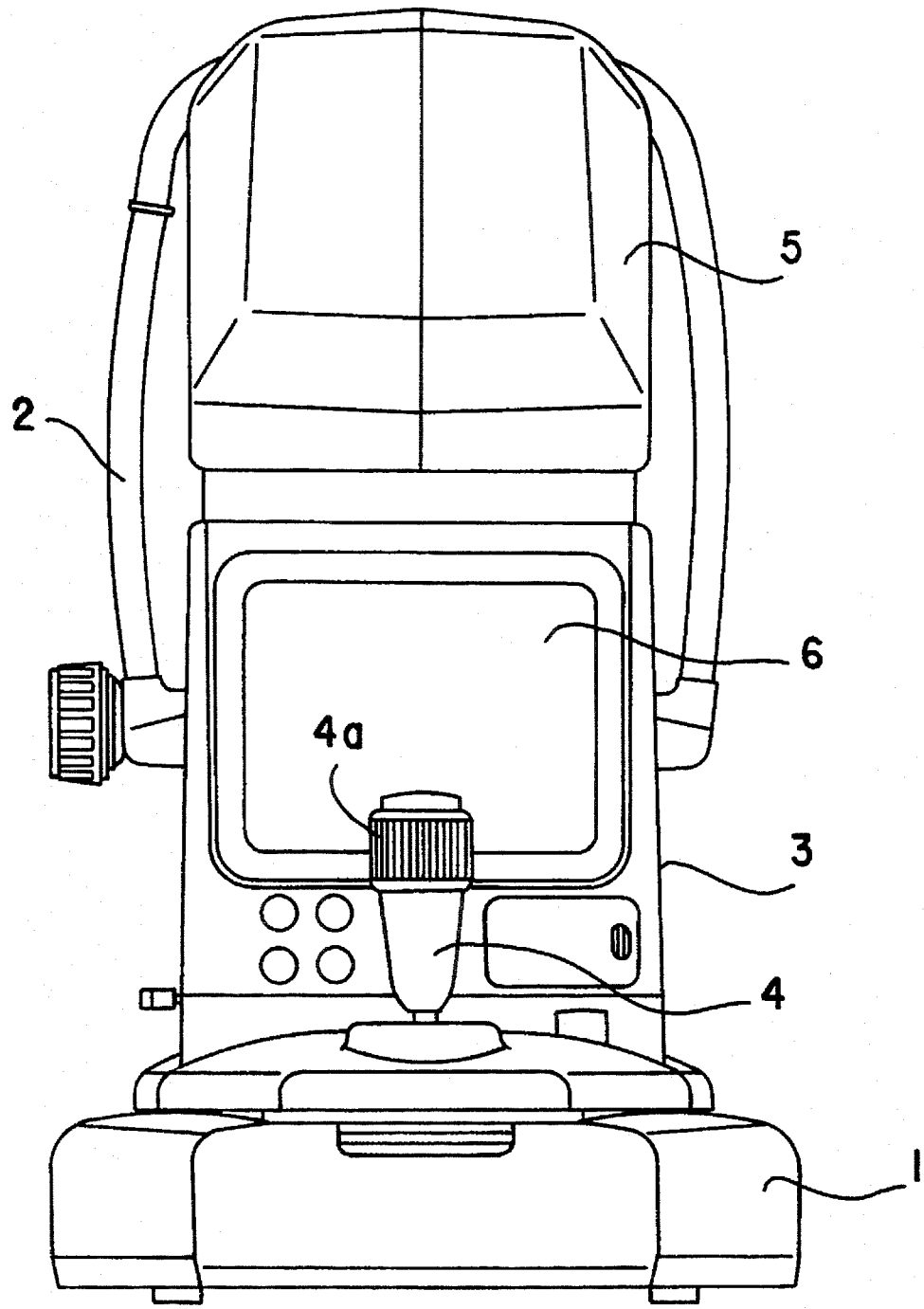
FIG. 1 is a front view of an ophthalmologic alignment device of an embodiment as viewed from the side of the user.
Figure 2:
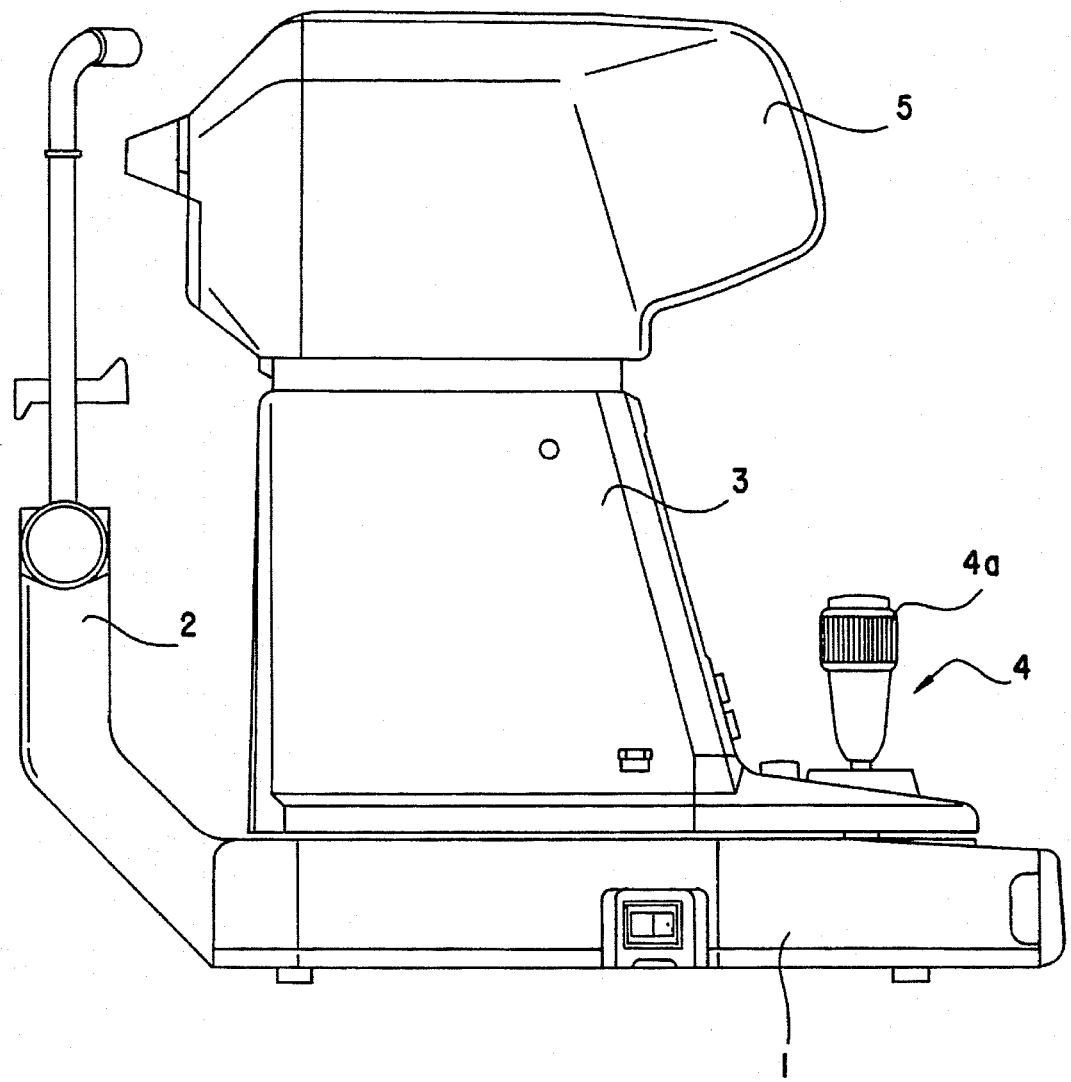
FIG. 2 is a left-hand side view of the device of FIG. 1.

Referring to FIGS. 1 and 2, a base 1 has a jaw base 2 which fixes patent's eyes. A device body 3 is slidable horizontally right and left, and back and forth on the base 1. The device body 3 is moved on the base 1 by the manipulation of a joystick 4. A measurement unit 5 receives a measuring system 5a (FIG. 6) and an optical system to be described later and further is moved vertically relative to the device body 3 by the user's manipulation of a rotary knob 4a provided on the joy stick 4.

Figure 3:
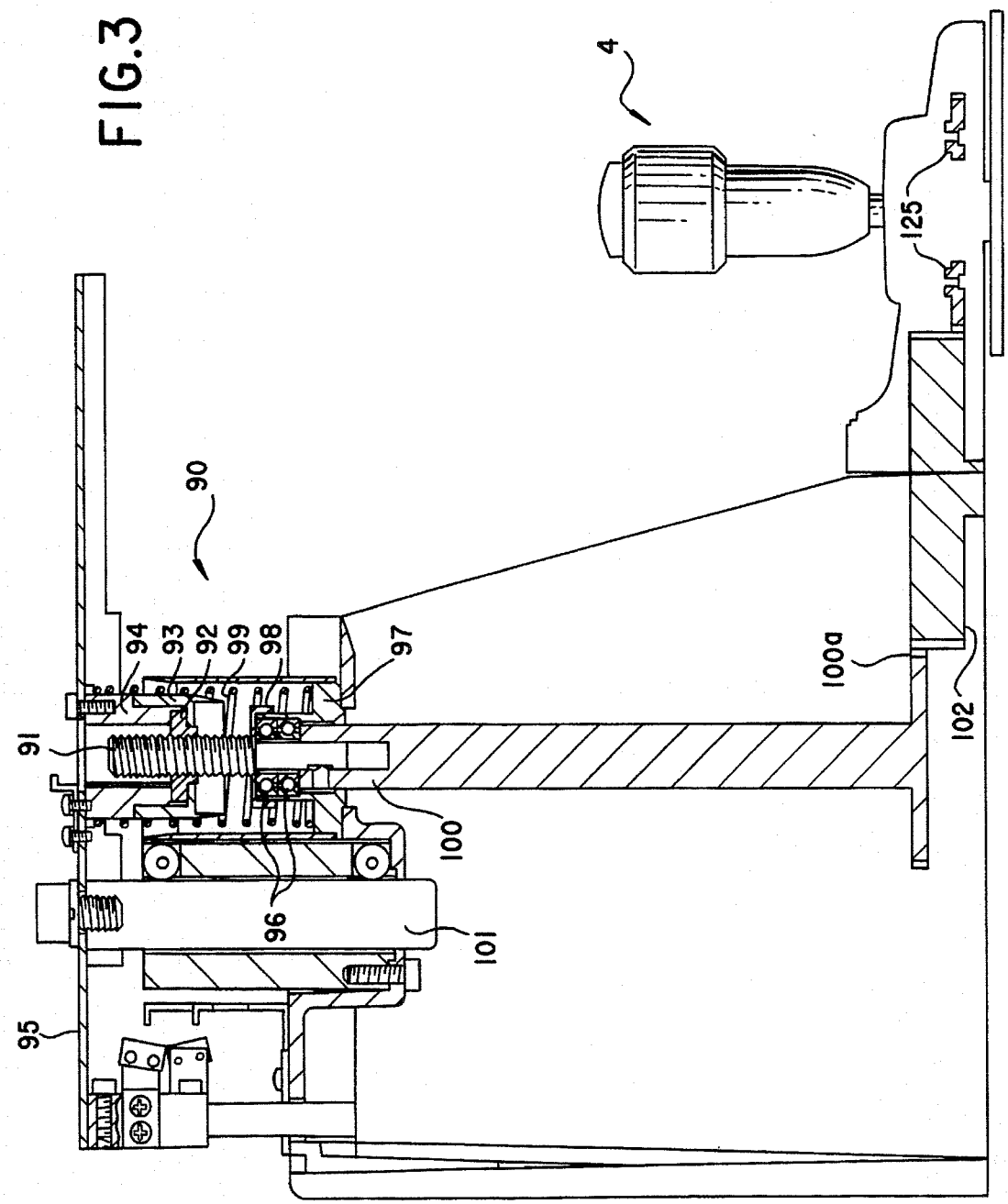
FIG. 3 shows a mechanism which moves an optical system of the device vertically.

Referring to FIG. 3, a vertical movement mechanism 90 for the optical system will be described. A male feed screw 91 is threadedly received in a female screw 92 held between a support 93 and a screw receiver 94, which is fixed to a support plate 95. The male screw 91 is also supported at a non-threaded portion thereof by ball bearings 96, a bearing receiver 97 and a bearing holder 98 which, in turn, are supported on a rotary shaft 100 with a compressed spring 99 being provided coaxially with the rotary male screw 91 between the plate 95 and the bearing receiver 97 to support the weight of the optical system, etc., and to ensure its smooth vertical movement. The female screw support 93 also functions as a guide for the compressed spring 99.

The rotation of gear 125 to be described later in more detail is transmitted to a gear 100a through a gear 102 to thereby rotate the rotary shaft and hence the male feed screw 91 and hence move the female screw 92 along with the female screw support 93, screw receiver 94 and plate 95 as a unit vertically along the grooves of the male screw 91.

Reference numeral 101 denotes a vertical movement guide shaft.

Figure 4:
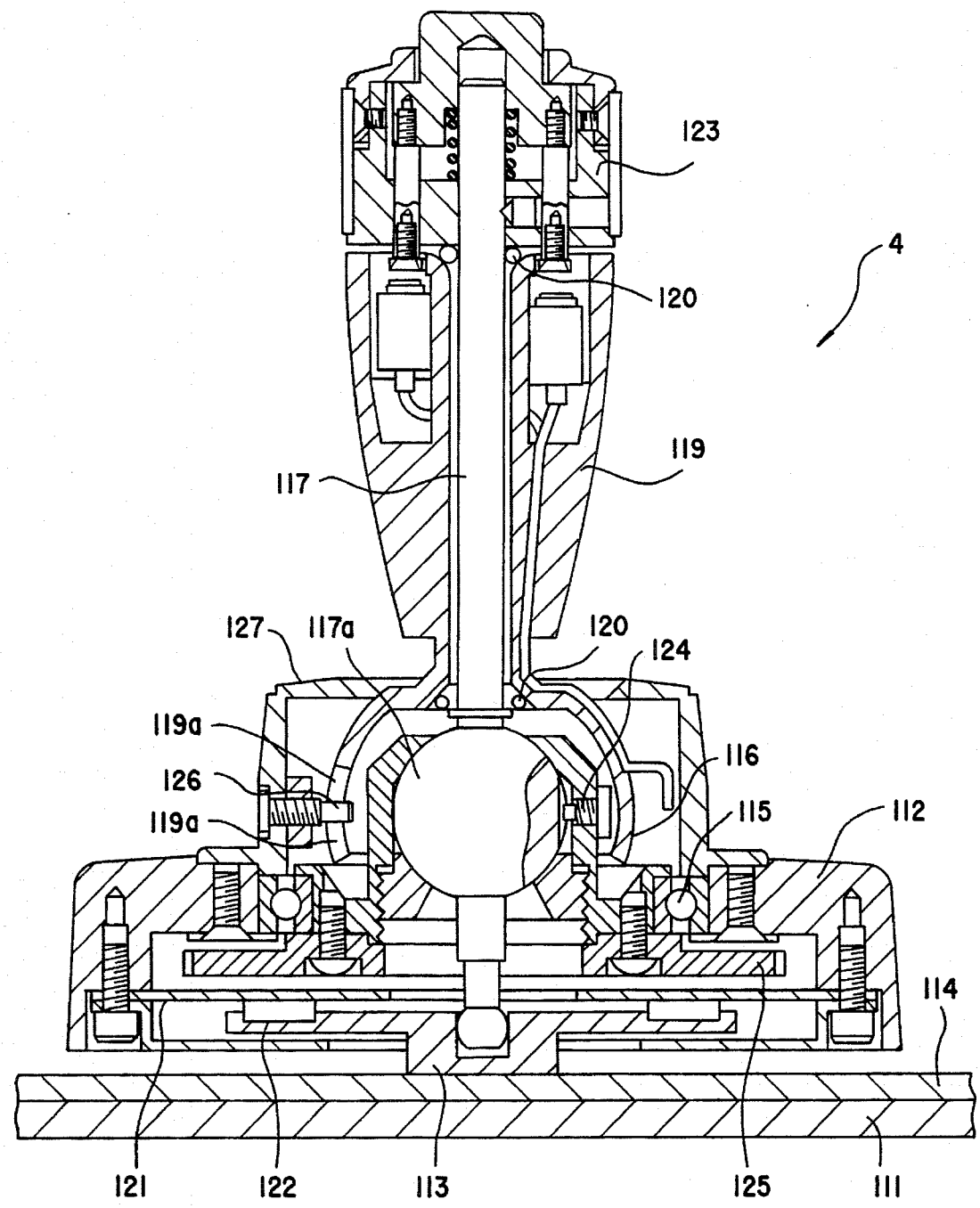
FIG. 4 is a cross-sectional view of a joystick preferred for use with the embodiment.

The structure of the joystick 4 will be described with reference to FIG. 4. The joystick 4 is used to move the measuring unit 5 to preform rough alignment. A base 112 is movable horizontally through a slider 113 on a frictional plate 114 supported on a fixed base 111. The base 112 supports the measuring unit 5 through the vertical movement mechanism 90. Provided through a ball bearing 115 on the base 112 is a housing 116 within which a lower spherical body 117a of stem 117 is engaged with a key 24. When a rotary knob 119 of the joystick 4 is rotated, the stem 117 is rotated through a ball bearing 120 with spherical body 117a as a fulcrum within the housing 116. Thus, the stem 117 swings the slider 113 at the lower end thereof. The frictional force between the sliding portion 113 and the frictional plate 114 is selected so as to be higher than that between a plate 121 fixed to the base 112 and a sliding plate 122 embedded in the slider 113. Thus, when the stem 117 swings the sliding plate 122 at the lower end thereof, the slider 113 does not move, but the base 112 slides on the sliding plate 122 horizontally slightly through the plate 121.

By rotating a rotary knob 123 fixed to an upper end of the stem 117, the stem 117 is rotated to thereby rotate the housing 116 through the key 124. A gear 125 fixed to the housing 116 transmits its torque to the vertical movement mechanism 90 which vertically moves the optical system. In the knob 119, a horizontal pin 126 is fixed to an upper cover 127 which, in turn, is fixed to the base 112 so as to extend toward the center of the spherical body 117a into a slot 119a provided in a lower end portion of the knob 119 to thereby free the knob 119 from rotation.

The measuring unit 5 is movable by about 5 mm right and left and back and forth relative to the device body 3 for automatic alignment. Reference numeral 6 denotes a TV monitor which displays information on the frontal eye image to be reported to the user.

[Structures of the Main Elements]

The main elements of the inventive device will be described next. The non-contact tonometer operates to inject a compressed air against the cornea of a respective one of the eyes to be examined to deform same so as to assume a predetermined state, to measure the air pressure directly or indirectly at that time, and to measure the intraocular pressure on the basis of the measured air pressure. The measuring mechanism of the non-contact tonometer itself has no important relationship to the present invention and further description thereof will be omitted.

Optical Alignment System

Figure 5:
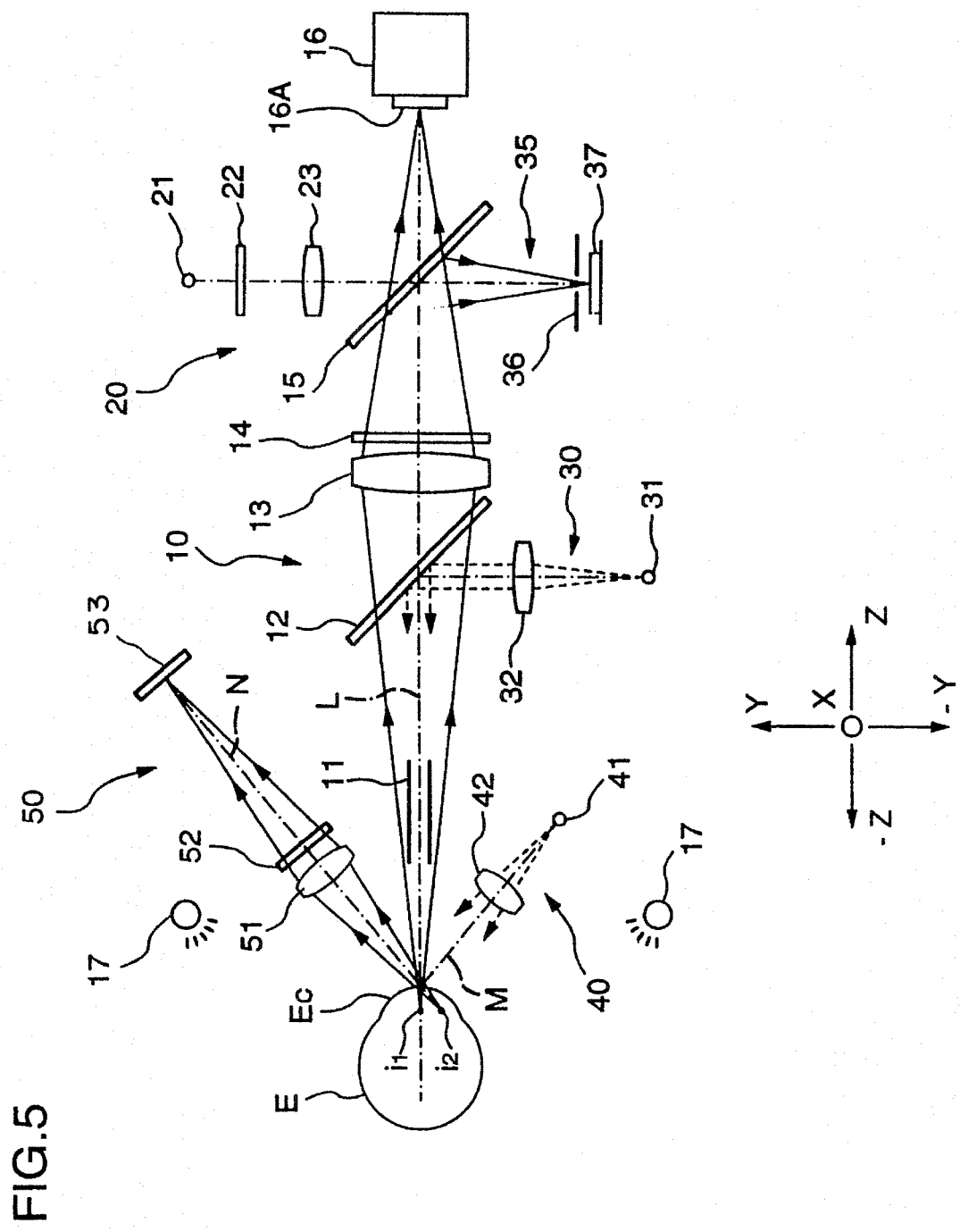
FIG. 5 is a top plan view of an optical alignment system of the embodiment.

FIG. 5 is a top plan view of an optical alignment system of the alignment device of the embodiment, which is composed of an optical observation unit 10, an optical reticle projection unit 20, an optical front index projection unit 30, an optical index detection unit 35, an optical distance projection unit 40, and an optical distance index detection unit 50, which will be described below.

(Optical Observation Unit 10)

A nozzle 11 which injects a gas which deforms a cornea is disposed on an optical path of the observation unit 10 such that the axis of the nozzle 11 aligns with an optical axis L of the observation unit 10. Disposed on the optical axis L are a half mirror 12, an objective 13, a filter 14, a half mirror 15 and a TV camera 16. The filter 14 has a characteristic which allows the wavelength of a luminous flux from the front index projection unit 30 to transmit therethrough, but does not allow the wavelength of a luminous flux from the distance index projection unit 40 to transmit therethrough and which prevents unnecessary luminous noise from reaching the TV camera 16 and a detector 37 of the optical index detection unit 35.

The frontal image of a respective one E of the eyes illuminated by near infrared radiations emitted from a turned-on eye observation illumination source 17 is imaged onto an image pickup plane 16A of the TV camera 16 through the half mirror 12, objective 13, filter 14, and half mirror 15 to appear on the TV monitor 6.

(Optical Reticle Projection Unit 20)

The optical reticle projection unit 20 is composed of a light source 21, a reticle disc 22 on which a ring-like mark is formed, and a projection lens 23. The reticle on the reticle disc 22 illuminated by the light source 21 is imaged onto the image pickup plane 16A of the TV camera 16 through the half mirror 15 and the projection lens 23 to appear overlapping with the frontal eye image on the TV monitor 6.

(Optical Front Index Projection Unit 30)

The front index projection unit 30 is composed of a projection lens 32 and a light source 31 which emits through the projection lens 32 an luminous flux, for example, close in wavelength to the near infrared radiations from the illumination light source 17.

The output of the light source 31 is modulated with a predetermined frequency to prevent the luminous flux from the illumination source 17 from acting as noise on the front index detection unit 35.

The radiations from the light source 31 are collimated, as shown by broken lines in FIG. 5, by the projection lens 32 and reflected by the half mirror 12 to pass through the nozzle 11 along the light axis L to be illuminated onto the cornea Ec. The luminous flux is then reflected by the cornea Ec to form on the eye E an index il as a virtual image of the light source 31. The luminous flux representing the index il forms an image of the index il on the image pickup plane 16A of the TV camera 16.

(Optical Front Index Detection Unit 35)

The optical front index detection unit 35 is composed of a field stop 36, a two-dimensional position detector 37 and the objective lens 13, filter 14 and half mirror 15, those last three elements being shared with the observation unit 10. The aperture diameter of the field stop 36 is selected such that no useless light impinges on the detector 37, but the luminous flux representing the index il at a substantially appropriate position relative to the position of the reticle image on the TV camera 16 enters the detector 37. The two-dimensional position detector 37 may include any one of various sensors such as a CCD and a PSD. Alternatively, a two- or four-division photodetector may be used in place of the two-dimensional position detector 37.

The luminous flux representing the front index reflected on the cornea Ec is guided by the half mirror 15 to the front index detection unit 35 and thence through the field stop 36 to the photodetector 37, which detects the position of the eye in the x, y and z directions relative to the optical measurement or observation axis L on the basis of the two-dimensional position of the luminous flux representing the index il and entering the photodetection surface of the photodetector 37.

As described above, the optical front index projection unit 30 and the front index detection unit 35 achieve alignment of the eye examination device with the eye E in the x and y directions, using the index il.

(Optical Distance Index Projection Unit 40)

In the distance index projection unit 40, an optical axis M is slanted relative to the optical axis L. The optical axis M intersects with the optical axis L at a position remote by a predetermined distance from the nozzle 11. Preferably, the optical axis M intersects with the optical axis L at an angle of 20–40 degrees. Provided on the optical axis M are a projection lens 42 and a light source 41 which emits through the projection lens 42 a luminous flux different in wavelength from that from the light source 31.

The luminous flux from the light source 41 is collimated by the projection lens 42, as shown by broken lines in FIG. 5, and illuminated along the optical axis M onto the cornea Ec. The luminous flux reflected by the cornea Ec forms on the eye an index i2 as an vertual image of the light source 41.

(Optical Distance Index Detection Unit 50)

In the distance index detection unit 50, an optical axis N is symmetrical with the optical axis M around the optical axis L. That is, the optical axis N intersects with the optical axis M on the optical axis L. Provided on the optical axis N are a photodection lens 51, filter 52, and one-dimensional detector 53. The filter 52 has a characteristic which allows luminous flux from the light source 41 of the distance index projection unit 40 to transmit therethrough, and which does not allow the luminous flux from the illumination source 17 and the light source 31 of the front index projection unit 30 to transmit therethrough and which prevents the luminous flux representing the index il and the luminous flux from the illumination source 17 from entering the one-dimensional detector 53 to become noise.

The luminous flux from the light source 41 reflected by the cornea and forming the index i2 impinges on the one-dimensional detector 53 through the lens 51 and the filter 52. When the eye to be examined moves in the direction of extension of the optical axis L, the image of the index i2 formed by the photodetection lens 51 also moves in the direction of detection of the one-dimensional detector 53. The position of the eye in the z (or back-fourth) direction is detected on the basis of a deviation of the index image on the one-dimensional detector 53.

A cylindrical lens whose generator which extends in the direction of detection of the one-dimensional detector 53 may be disposed before the one-dimensional detector 53.

As described above, the optical distance index projection unit 40 and the optical distance index detection unit 50 achieve alignment of the eye examination device with the eye in the z direction, using the index i2.

Control System

FIG. 6 is a block diagram of the essential portion of a control system according to the present invention. Signals output from the two- and one-dimensional position detectors 37 and 53 are subjected to predetermined processing by corresponding detection processors 60 and 61, and then input to a controller 62, which processes those signals in a well-known manner to provide a signal indicative of deviations (in the x, y and z directions in FIG. 5) of the eye to be examined E from a reference position.

As shown in FIG. 6, an x driver 63 moves the measuring unit 5 vertically relative to the observation axis L (or in the x direction). A y driver 64 moves the measuring unit 5 horizontally relative to the observation axis L (or in the y direction). A z driver 65 moves the measuring unit 5 along the observation axis L (or in the z direction). Those drivers each are composed of a motor and a motor drive unit which operates on the basis of a signal obtained by the controller 62 indicative of a deviation from the corresponding direction. An automatic/manual alignment switch 66 is used to switch between automatic and manual alignment operations.

A character display 67 generates a signal indicative of a figure/character for aligning purposes. A synthesizer 68 synthesizes a video signal from the TV camera 16 and a signal from the character display 67.

A signal indicative of a deviation of the eye in the z direction from the controller 62 is delivered to the character display 67, which generates a predetermined figure signal and a position signal on the TV monitor 6 on the basis of the delivered signal. The synthesizer 68 synthesizes the signals from the character display 67 and the video signal from the TV camera 16 into a synthetic signal, which is then input to the TV monitor 6. Reference numerals 70, 71, 72 and 73 denote a frontal image of the eye, a reticle image, a front index image and a distance mark composed of signals from the character display 67, respectively, on the TV monitor 6. The distance mark 73 moves the reticle image 71 vertically on the TV monitor 6 on a real time basis in correspondence to the distance from the nozzle 12 to the cornea Ec. When the cornea Ec is at an appropriate working distance, the distance mark 73 aligns with the reticle image 71.

Reference numerals 80, 81 and 82 denote a timer, a buzzer, and a driver for the buzzer, respectively.

The operation of the alignment device will be described next with reference to a flowchart of FIG. 7.

The user positions the eye to be examined E at a predetermined position relative to the jaw base 2 and turns on the power supply switch (not shown) to thereby light up the respective light sources. A frontal image of the eye to be examined E illuminated by the turned-on illumination light source 17 is received by the TV camera 16 through the observation unit 10 along with a reticle image produced by the reticle projection unit 20 to appear on the TV monitor 6.

The alignment switch 66 is operated to select one of automatic and manual alignment modes.

When the automatic alignment mode is selected, the user manipulates the joystick 4 and the rotary knob 4a to align the ring-like reticle image 71 roughly with the iris or pupil of the eye to make a focusing adjustment such that the index il is minimized in size, while viewing the frontal eye image 70 and the reticle image 71 on the TV monitor 6.

When a luminous flux representing the index il enters the two-dimensional detector 37 of the optical detection unit 35 and the image pickup plane of the TV camera 16, so that the TV camera catches the index il image, a front index image 72 appears on the TV monitor 6. When a luminous flux representing the index i2 enters the one-dimensional detector 53 of the optical detection unit 50, a distance mark 73 appears on the TV monitor 6. The user views those the displayed images to find the completion of rough alignment. In this case, the completion of rough alignment may be indicated in a separate manner on the basis of the signals from the two- and one-dimensional detectors 37 and 53.

When the rough alignment is thus completed, the manipulation of the joystick 4 ends, and automatic alignment is performed. In the automatic alignment, the controller 62 obtains deviations (in the x, y and y directions) of the eye E from its reference position on the basis of the output signals from the two- and one-dimensional detectors 37 and 53, and operates the x, y and z drivers 63, 64 and 65 on the basis of the corresponding signals indicative of those deviations. When the measuring unit 5 moves relative to the device body 3 in response to those operations of the drivers, the index images of the two- and one-dimensional detectors 37 and 53 move accordingly, and the controller 62 determines whether the respective index images are in the allowable range of alignment completion.

When the controller 62 performs the automatic alignment, it reads the time when its operation started from the timer 80 and performs a timekeeping operation. Then, when the controller 62 determines that the results of the detection of the detectors 37 and 53 are in the predetermined allowable range in a predetermined time after the start of the automatic alignment, the controller 62 generates a signal to stop the respective drivers and to automatically operate the measuring system 5a to perform the measurement (or the user depresses a measurement starting switch (not shown) to start the measurement after the user receives a message or the like indicative of the completion of the alignment).

If the movement of the device cannot follow up the movement of the eye, for example, owing to flicks of the eye even when the automatic alignment has been is performed, and if no alignment is performed in the predetermined range in the predetermined time after the start of the automatic alignment, the controller 62 relieves control over the respective drivers and causes the buzzer 81 to generate an alarm sound through the drive unit 82 to thereby inform the user that the alignment mode has been switched from the automatic one to the manual one.

When the user knows this switching of the alignment mode, he performs the manual alignment operation as follows:

When the user completes rough alignment, the frontal eye image 70, the reticle image 71, the front index image 72 and the distance mark 73 appear on the TV monitor 6. For vertical and horizontal position adjustment of the front index image, the user manipulates the joystick 4 and the rotary knob 4a to put the front index image 72 into the ring-like reticle image 71. For back and forth position adjustment of the front index image, the user slants the joystick 4 back and forth to align the distance mark 73 with the reticle image 71.

When the controller 62 determines that the results of the detection of the detectors 37 and 53 are in the predetermined allowable range owing to the manual alignment, the controller 62 generates a signal which operates the measuring system 5a to cause same to perform its measurement. In this case, the measuring system 5a may start its measurement in response to the user's operation of a measurement starting switch (not shown).

While the embodiment has illustrated the automatic switching of the automatic alignment to the manual alignment when the results of the detection are not in the predetermined range even after the lapse of the predetermined time since the start of the automatic alignment, the automatic alignment may continue by resetting the allowable range of alignment at a one with a lower accuracy when the results of the detection are not in the predetermined range even after the lapse of the predetermined time.

The operation of the alignment device performed when allowable ranges with a higher and a lower accuracy are provided will be described with respect to FIGS. 8 and 9.

When the user has completed lower-accuracy alignment in the manner described above, the device drives the respective drivers to perform an automatic alignment operation with a higher accuracy. Therefore, if the alignment is not completed in the predetermined time after the automatic alignment started, the controller 62 determines whether the alignment accuracy selection switch has selected automatic alignment with a lower accuracy. If not, the controller 62 causes the buzzer 81 to generate an alarm sound and switches the alignment operation from the automatic one to the manual one.

When the automatic alignment with a lower accuracy has been selected, the controller 62 determines whether the alignment with a lower accuracy has been completed in the allowable range with the preset lower accuracy. If so, the controller 62 stops control over the respective drers involved in the automatic alignment and performs the measurements with a lower accuracy. The results of the measurements are displayed as ones with a lower accuracy on the TV monitor 6.

The controller 62 reads from the timer 80 the time elapsed since the allowable range with a lower accuracy has been selected, and continues the measurement. When the automatic alignment with a lower accuracy is not completed in the predetermined time, the controller 62 causes the buzzer 81 to generate an alarm sound and selects the manual alignment, as mentioned above.

While in the embodiment the alignment accuracy selection switch has been illustrated as selecting the automatic alignment with a lower accuracy, the switch is not necessarily required to be provided. When alignment with a higher accuracy cannot be achieved, lower accuracy alignment may instead be selected automatically.

While the alignment accuracy has been illustrated as including two higher and lower ones, it may include more accuracies as required.

While in the embodiment whether the alignment state is in the predetermined allowable range is determined on the basis of the position detection of the detectors 37 and 57, it may be determined in dependence on the luminous amounts of the index images present when the detectors 37 and 53 detect the index images.

As described above, according to the present invention, the alignment operation is switchable between the automatic and manual ones in dependence on the state of the eye to be examined. Thus, the measurement is facilitated.

When the automatic alignment is difficult, the manual alignment is selected automatically. Thus, the user is able to perform an optimal measurement without spending any unnecessary time and imposing any excess load on the eye.

In the present invention, by preparing a plurality of different allowable ranges of alignment, the automatic alignment with a lower accuracy is performed automatically on the eye on which automatic alignemnt is difficult to preform. Thus, measurement is achieved by further making the most of the function of the automatic alignment.

What is claimed is:

1. An ophthalmologic alignment device for aligning a measuring system at a predetermined position for an eye to be examined, comprising:

observation means for observing the front of the eye;

first moving means for moving the measuring system with a joystick for aligning purposes while observing the eye with said observation means;

second moving means for further moving the measuring system moved by said first moving means;

index projection/detection means for projection an index onto the cornea of the eye and detecting index light reflected by the cornal surface;

drive/control means for driving/controlling said second moving means on the basis of a detection result of said index projection/detection means;

mode switching means for switching an alignment mode in which the measuring system is moved from a one in which the measuring system is moved by said first moving means to a one in which the measuring system is moved by said second moving means; and informing means for informing an operator of that an operation of the second moving means has started after detecting as to whether the index is located within a predetermined region based on the detection result due to the index projection/detection means.

2. An ophthalmic alignment device according to claim 1, wherein said index projection/detection means comprises:

an optical first index projection unit for projecting a first against the cornea of the eye, an optical first detection unit for detecting the first index, an optical second index projection unit for projecting a second index against the cornea of the eye, the second index projection unit having an optical axis intersecting with an optical axis of said first index projection unit, and an optical second detection unit for detecting the second index.

3. An ophthalmic alignment device according to claim 2, wherein at least one of said first and second detection units comprises a two-dimensional position detector.

4. An ophthalmic alignment device according to claim 2, wherein said first detection unit comprises a mirror provided in an optical path of an optical system of said observation means for reflecting a luminous flux representing the first index and transmitting the luminous flux in the optical system of said observation means through said mirror, and photodetection means disposed in an optical path diverged by said mirror.

5. An ophthalmic alignment device according to claim 1, further comprising reporting means for reporting to the user data on the alignment based on the result of the detection of said index projection/detection means when said first moving means moves the measuring system for aligning purposes.

6. An ophthalmic alignment device according to claim 5, wherein said reporting means comprises display means for displaying a mark which indicates the direction of moving said measuring system.

7. An ophthalmic alignment device according to claim 5, further comprising means for stopping the operation of said drive/control means.

8. An ophthalmic alignment device according to claim 7, wherein said stopping means comprises a selection switch for selecting the direction of movement of the measuring system by said second moving means.

9. An ophthalmologic alignment device for aligning a measuring system at a predetermined position for an eye to be examined, comprising:

observation means for observing the front of the eye;

first moving means for moving the measuring system with a joystick for aligning purposes while observing the eye with said observation means;

second moving means for further moving the measuring system moved by said first moving means;

index projection/detection means for projection an index onto the cornea of the eye and detecting index light reflected by the cornal surface;

drive/control means for driving/controlling said second moving means on the basis of a detection result of said index projection/detection means;

mode switching means for switching an alignment mode in which the measuring system is moved from a one in which the measuring system is moved by said first moving means to a one in which the measuring system is moved by said second moving means;

measuring means for measuring an alignment time taken for said second moving means to move the measuring system;

determining means for determining whether the result of detection of said index projection/detection means is in a predetermined allowable range and hence whether the alignment of the measuring system with the eye has been completed; and returning means for returning the alignment mode to the alignment mode in which the measuring system is moved by said first moving means when said determining means determines that the alignment of the measuring system with the eye has not been completed in the predetermined time.

10. An ophthalmic alignment device according to claim 9, further comprising means for specifying that the alignment mode has been returned to that for said first moving means.

* * * * *